United States Patent [19]

Rosentreter et al.

[11] Patent Number: 4,843,091
[45] Date of Patent: Jun. 27, 1989

[54] INDOLYLPROPIONIC ACIDS, COMPOSITIONS OF, AND USE THEREOF TO INHIBIT THROMBOCYTE AGGREGATION

[75] Inventors: Ulrich Rosentreter, Wuppertal; Horst Böshagen, Haan; Folker Lieb, Leverkusen; Hermann Oediger, Cologne; Volker-Bernd Fiedler, Leverkusen; Elisabeth Perzborn; Friedel Seuter, both of Wuppertal, all of Fed. Rep. of Germany

[73] Assignee: Bayer Aktiengesellschaft, Leverkusen, Fed. Rep. of Germany

[21] Appl. No.: 58,489

[22] Filed: Jun. 5, 1987

[30] Foreign Application Priority Data

Jun. 28, 1986 [DE] Fed. Rep. of Germany ....... 3621761

[51] Int. Cl.[4] ................. C07D 209/04; A61K 31/405
[52] U.S. Cl. .................................... 514/419; 548/494; 548/469
[58] Field of Search ................. 548/494, 469; 514/419

[56] References Cited

U.S. PATENT DOCUMENTS 3,472,870 10/1969 Larsen et al. ...................... 548/494

FOREIGN PATENT DOCUMENTS 0155828 9/1985 European Pat. Off. .
1172320 11/1987 United Kingdom ................ 548/494

OTHER PUBLICATIONS

Chemical Abstracts, Band 94, 11.–25. Mai 1981, Columbus, Ohio, USA.
Lagidze, D. et al., "Synthesis of Some New Analogs of Melatonin and B-Carboline from 4-phenylpentanoic Acid", Seite 637, Spalte 1, Zusammenfassung-Nr. 156 681z.
Izv. Akad. Nauk Gruz. SSR, Ser. Khim. 1980, 6(3), 225–231.

*Primary Examiner*—David B. Springer
*Attorney, Agent, or Firm*—Sprung Horn Kramer & Woods

[57] ABSTRACT

An N-sulphonamidoethyl-indole of the formula

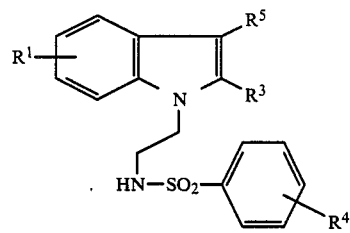

in which
$R^1$ represents hydrogen, alkyl, alkoxy, alkylthio, halogen, trifluoromethyl, trifluoromethoxy, trifluoromethylthio, difluoromethoxy, aryl, arylthio, aralkyl, aralkoxy, aralkylthio, acyl or a group of the formula

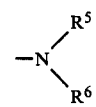

in which
$R^5$ and $R^6$ are identical or different and denote hydrogen, alkyl, aryl, aralkyl or acyl, and
$R^3$ represents hydrogen, alkyl, aryl, pyridyl, thienyl or furyl, and
$R^4$ represents hydrogen, alkyl, alkoxy, alkylthio, halogen, trifluoromethyl, trifluoromethoxy, trifluoromethylthio, aryl, aryloxy, arylthio, aralkyl, aralkoxy, aralkylthio, acl or a group of the formula

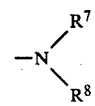

in which
$R^7$ and $R^8$ are identical or different and denote hydrogen, alkyl, aryl, aralkyl or acyl,
$R^5$ represents hydrogen,

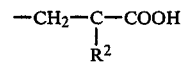

or a pharmacologically acceptable salt of

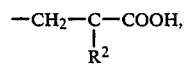

and
$R^2$ represents hydrogen, alkyl or aryl.
The compounds were $R^5$ is

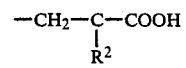

or a salt thereat inhibit the aggregation of thrombacytes.

10 Claims, No Drawings

INDOLYLPROPIONIC ACIDS, COMPOSITIONS OF, AND USE THEREOF TO INHIBIT THROMBOCYTE AGGREGATION

The invention relates to new indolypropionic acids, processes for their preparation, and their use in medicaments New indolypropionic acids of general formula (I)

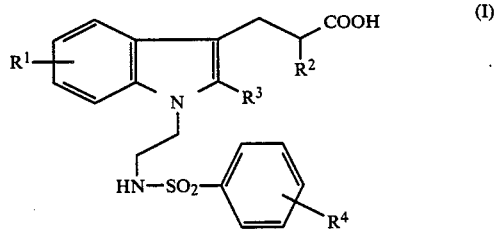

in which
R$^1$ represents hydrogen, alkyl, alkoxy, alkylthio, halogen, trifluoromethyl, trifluoromethoxy, trifluoromethylthio, difluoromethoxy, aryl, aryloxy, arylthio, aralkyl, aralkoxy, aralkylthio acyl or a group of the formula

in which
R$^5$ and R$^6$ are identical or different and denote hydrogen, alkyl, aryl, aralkyl or acyl,
R$^2$ represents hydrogen, alkyl or aryl,
R$^3$ represents hydrogen, alkyl, aryl, pyridyl, thienyl or furyl, and
R$^4$ represents hydrogen, alkyl, alkoxy, alkylthio, halogen, trifluoromethyl, trifluoromethoxy, trifluoromethylthio, aryl, aryloxy, arylthio, aralkyl, aralkoxy, aralkylthio, acyl or a group of the formula

in which
R$^7$ and R$^8$ are identical or different and denote hydrogen, alkyl, aryl, aralkyl or acyl,
and the salts thereof have been found.

The indolypropionic acids according to the invention may also be present in the form of their salts. In general, salts with organic or inorganic bases may be mentioned here.

In the context of the present invention, physiologically acceptable salts are preferred. Physiologically acceptable salts of the indolypropionic acids may be metal or ammonium salts. Sodium, potassium, magnesium or calcium salts, and also ammonium salts which are derived from ammonia or organic amines, such as, for example, ethylamine, diethylamine, triethylamine, diethanolamine, triethanolamine, dicyclohexylamine, dimethylaminoethanol, arginine or ethylenediamine, for example, are particularly preferred.

Surprisingly, the substances according to the invention exhibit a thrombocyte aggregation-inhibiting action and may be used for the therapeutic treatment of humans and animals.

In general, alkyl represents a straight chain or branched hydrocarbon radical having 1 to 12 carbon atoms. Lower alkyl having 1 to about 6 carbon atoms is preferred. An alkyl radical having 1 to 4 carbon atoms is particularly preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, alkoxy represents a straight-chain or branched hydrocarbon radical having 1 to 12 carbon atoms and bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general, alkylthio represents a straight-chain or branched hydrocarbon radical, having 1 to 12 carbon atoms, which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, oxtylthio or isooctylthio.

In general, aryl represents an aromatic radical having 6 to about 12 carbon atoms. Preferred aryl radicals are phenyl, naphthyl and biphenyl.

In general, aryloxy represents an aromatic radical, having 7 to about 12 carbon atoms, which is bonded via an oxygen atom. Preferred aryloxy radicals are phenoxy or naphthyloxy.

In general, arylthio represents an aromatic radical, having 6 to about 12 carbon atoms, which is bonded via a sulphur atom. Preferred arylthio radicals are phenylthio or naphthylthio.

In general, aralkyl represents an aryl radical, having 7 to 14 carbon atoms, which is bonded via an alkylene chain. Preferred aralkyl radicals are those having 1 to 6 carbon atoms in the aliphatic part and 6 to 12 carbon atoms in the aromatic part. The following aralkyl radicals may be mentioned as examples: benzyl, naphthylmethyl, phenethyl and phenylpropyl.

In general, aralkoxy represents an aralkyl radical having 7 to about 14 carbon atoms, the alkyl chain being bonded via an oxygen atom. Preferred aralkoxy radicals are those having 1 to 6 carbon atoms in the aliphatic part and 6 to 12 carbon atoms in the aromatic part. The following aralkoxy radical may be mentioned as examples: benzyloxy, napthylmethoxy, phenethoxy and phenylpropoxy.

In general, aralkylthio represents an aralkyl radical having 7 to about 14 carbon atoms the alkyl chain being bonded via a sulphur atom. Preferred aralkylthio radicals are those having 1 to 6 carbon atoms in the aliphatic part and 6 to 12 carbon atoms in the aromatic part. The following aralkylthio radicals may be mentioned as examples: benzylthio, naphthylmethylthio, phenethylthio and phenylpropylthio.

In general, acyl represents phenyl or straightchain or branched lower alkyl, having 1 to about 6 carbon atoms, which is bonded via a carbonyl group. Phenyl or alkyl radicals having up to 4 carbon atoms are preferred. Examples which may be mentioned are: benzoyl, acetyl, ethylcarbonyl, propylcarbonyl, isopropylcarbonyl, butylcarbonyl, isobutylcarbonyl.

In general, halogen represents fluorine, chlorine, bromine or iodine, preferably fluorine, chlorine or bromine. Halogen particularly preferably represents fluorine or chlorine.

Preferred compounds of the general formula (I) are those in which $R^1$ represents hydrogen, lower alkyl, lower alkoxy, fluorine, chlorine, bromine, iodine, trifluoromethyl, trifluoromethoxy, phenyl, phenoxy, benzyl, phenethyl, benzyloxy, acetyl or a group of the formula

in which $R^5$ and $R^6$ are identical or different and denote hydrogen, lower alkyl, phenyl, benzyl or acetyl, $R^2$ represents hydrogen, lower alkyl or phenyl, $R^3$ represents hydrogen, lower alkyl or phenyl, and $R^4$ represents hydrogen, lower alkyl, lower alkoxy, fluorine, chlorine, bromine, trifluoromethyl, trifluoromethoxy, phenyl, phenoxy, benzyl, phenethyl, benzyloxy, acetyl or a group of the formula

in which $R^7$ and $R^8$ are identical or different and denote hydrogen, lower alkyl, phenyl, benzyl or acetyl and the salts thereof.

Particularly preferred such compounds of the general formula (I) are those in which $R^1$ represents hydrogen, $C_1$–$C_4$-alkyl, $C_1$–$C_4$-alkoxy, fluorine, chlorine, bromine, trifluoromethyl, $C_1$–$C_4$-alkylamino or di-$C_1$–$C_4$-alkylamino, $R^2$ represents hydrogen or $C_1$–$C_4$-alkyl, $R^3$ represents hydrogen, $C_1$–$C_4$-alkyl or phenyl, and $R^4$ represents hydrogen, $C_1$–$C_4$-alkyl, $C_1$–$C_4$-alkoxy, fluorine, chlorine, bromine, trifluoromethyl, $C_1$–$C_4$-alkylamino or di-$C_1$–$C_4$-alkylamino, and the salts thereof.

The following indolylpropionic acids may be mentioned as examples:

3-{1-[2-[(4-methylphenyl)sulphonamido]ethyl]indol-3-yl}propionic acid

3-{1-[2-[(4-fluorophenyl)sulphonamido]ethyl]indol-3-yl}propionic acid

3-{1-[2-[(4-chlorophenyl)sulphonamido]ethyl]indol-3-yl}propionic acid

3-{2-methyl-1-[2-[(4-fluorophenyl)sulphonamido]ethyl]indol-3-yl}propionic acid

3-{2-methyl-1-[2-[(4-chlorophenyl)sulphonamido]ethyl]indol-3-yl}propionic acid

3-{5-chloro-1-[2-[(4-fluorophenyl)sulphonamido]ethyl]indol-3-yl}propionic acid

3-{6-methoxy-1-[2-[(4-chlorophenyl)sulphonamido]ethyl]indol-3-yl}propionic acid

3-{1-[2-[(4-chlorophenyl)sulphonamido]ethyl]-2-phenyl-indol-3-yl}propionic acid

Furthermore, a process has been found for the preparation of indolypropionic acids of the general formula (I)

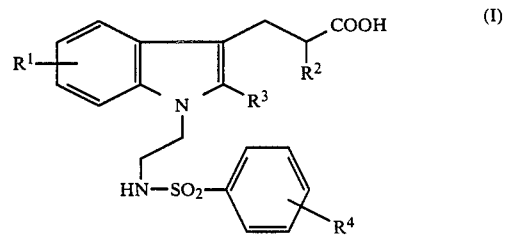

in which $R^1$ represents hydrogen, alkyl, alkoxy, alkylthio, halogen, trifluoromethyl, trifluoromethoxy, trifluoromethylthio, difluoromethoxy, aryl, aryloxy, arylthio, aralkyl, aralkoxy, aralkylthio, acyl or a group of the formula

in which $R^5$ and $R^6$ are identical or different and denote hydrogen, alkyl, aryl, aralkyl or acyl, $R^2$ represents hydrogen, alkyl or aryl, $R^3$ represents hydrogen, alkyl, aryl, pyridyl, thienyl or furyl, and $R^4$ represents hydrogen, alkyl, alkoxy, alkylthio, halogen, trifluoromethyl, trifluoromethoxy, trifluoromethylthio, aryl, aryloxy, arylthio, aralkyl, aralkoxy, aralkylthio, acyl or a group of the formula

in which $R^7$ and $R^8$ are identical or different and denote hydrogen, alkyl, aryl, aralkyl or acyl and the salts thereof, which is characterized in that N-sulphonamidoethyl-indols of the general formula (II)

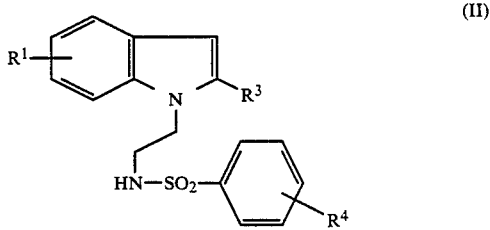

in which $R^1$, $R^3$ and $R^4$ have the meaning specified, are reacted with acrylic acids of the general formula (III)

in which

R² has the abovementioned meaning in inert solvents, and, in the case of the preparation of the salts, are reacted with an appropriate base.

The process according to the invention may be illustrated by the following equation:

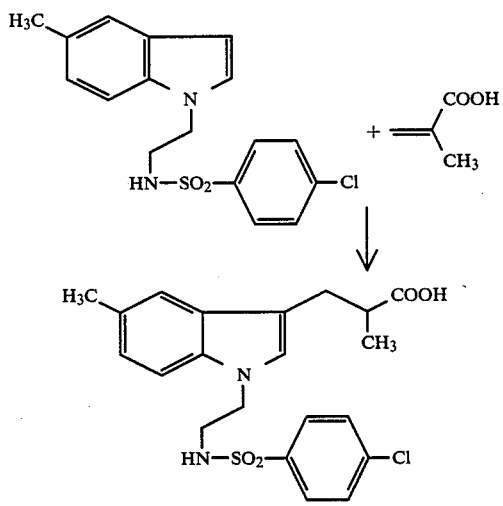

Suitable solvents for the process according to the invention are inert organic solvents which do not alter under the reaction conditions. These preferably include carboxylic acids, such as formic acid, acetic acid, propionic acid, trichloroacetic acid or trifluoroacetic acid, or carboxylic acid anhydrides, such as acetic anhydride, propionic anhydride or trifluoroacetic anhydride. It is likewise possible to employ mixtures of the solvents mentioned. A mixture of carboxylic acid and carboxylic acid anhydride is preferably employed, such as, for example, a mixture of acetic acid and acetic anhydride, or trifluoroacetic acid and trifluoroacetic anhydride.

The process is generally carried out in a temperature range from 0° C. to +150° C., preferably from +20° C. to +110° C.

The process according to the invention is generally carried out at atmospheric pressure. However, it is also possible to carry out the process at superatmospheric pressure or at subatmospheric pressure (for example in a pressure range from 0.5 to 5 bar).

In general, 1 to 6 moles, preferably 2.5 to 4 moles of the acrylic acid (III) are employed relative to 1 mole of the N-sulphonamidoethyl-indole (II).

In general, the indolypropionic acids (I) are converted into their salts by reacting the acids with conventional bases, if appropriate in inert solvents, such as, for example, water or alcohols, for example methanol, ethanol, propanol or isopropanol, or acetonitrile, dioxane, tetrahydrofuran or dimethylformamide, or mixtures thereof.

Bases which may be mentioned as examples are: alkali metal or alkaline earth metal oxides, hydroxides, carbonates or bicarbonates, for example sodium carbonate, potassium carbonate, sodium bicarbonate, potassium bicarbonate, sodium hydroxide, potassium hydroxide, calcium hydroxide or magnesium hydroxide, or ammonia or organic amines, such as, for example, ethylamine, diethylamine, triethylamine, diethanolamine, triethanolamine, dihexylamine or ethylenediamine.

The process according to the invention may be carried out, for example, as follows:

The N-sulphonamidoethyl-indole is dissolved in an inert solvent or solvent mixture, acrylic acid is added, and the mixture is warmed, if appropriate. When the reaction is complete, the mixture is worked up by extraction and/or chromatography.

The following are employed, for example, according to the invention as N-sulphonamidoethyl-indoles:
N-[2-(indol-1-yl)ethyl]-(4-methylphenyl)sulphonamide
N-[2-(indol-1-yl)ethyl]-(4-fluorophenyl)sulphonamide
N-[2-(indol-1-yl)ethyl]-(4-chlorophenyl)sulphonamide
N-[2-(2-methylindol-1-yl)ethyl]-(4-fluorophenyl)sulphonamide
N-[2-(2-methylindol-1-yl)ethyl]-(4-chlorophenyl)sulphonamide
N-[2-(5-chloroindol-1-yl)ethyl]-(4-fluorophenyl)sulphonamide
N-[2-(2-phenylindol-1-yl)ethyl]-(4-chlorophenyl)sulphonamide
N-[2-(6-methoxyindol-1-yl)ethyl]-(4-chlorophenyl)sulphonamide The acrylic acids of the formula (III) are known or can be prepared by known methods [Beilstein's Handbuch der organischen Chemie (Beilstein's Handbook of Organic Chemistry) 2, 397, 421].

The following may be used, for example, according to the invention as acrylic acids:
acrylic acid or methacrylic acid.

The N-sulphonamidoethyl-indoles of the general formula (II) are new.

They can be prepared by reacting indoles of the general formula (IV)

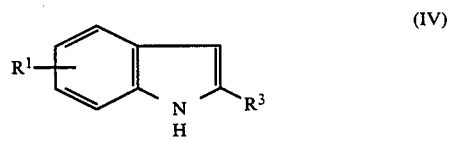

in which

R¹ and R³ have the abovementioned meaning with aziridines of the general formula (V)

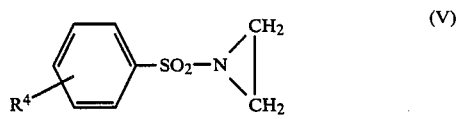

in which

R⁴ has the abovementioned meaning, in the presence of bases in inert solvents.

The preparation of the N-sulphonamidoethyl-indoles of the general formula (II) which are used as starting materials may be clarified by the following equation:

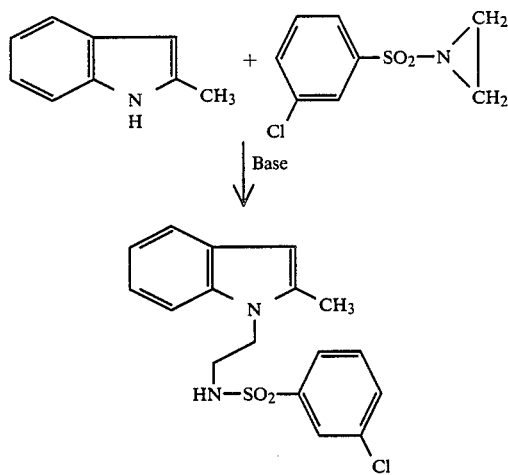

Inert organic solvents which do not alter under the reaction conditions may be used as solvents for the process. These preferably include ethers, such as, for example, diethyl ether, dioxane, tetrahydrofuran or glycol dimethyl ether, or hydrocarbons, such as, for example, benzene, toluene or xylene, or chlorinated hydrocarbons, such as, for example, dichloromethane, trichloromethane, tetrachloromethane or chlorobenzene, or amides, such as, for example, dimethylformamide or hexamethylphosphoric triamide, or dimethyl sulphoxide. It is likewise possible to employ mixtures of the solvents mentioned.

Suitable bases are the conventional basic compounds for basic reactions. These preferably include alkali metal or alkaline earth metal hydroxides, such as, for example, sodium hydroxide, potassium hydroxide or barium hydroxide, or sodium or potassium carbonates, such as, for example, sodium carbonate, sodium bicarbonate or potassium carbonate, or alkali metal alcoholates, such as, for example, sodium methanolate, potassium methanolate, sodium ethanolate, potassium ethanolate or potassium tert-butanolate, or alkali metal hydrides, such as, for example, lithium hydride, sodium hydride or potassium hydride, or alkali metal amides, such as, for example, sodium amide, potassium amide or lithium diisopropylamide, or organolithium compounds, such as, for example, n-butyllithium, tertbutyllithium or phenyllithium, or sodium hexamethylsilazane.

The process is generally carried out in a temperature range from $-80°$ C. to $+50°$ C., preferably from $-20°$ C. to $+20°$ C.

The process is generally carried out at atmospheric pressure. However, it is also possible to carry out the process at subatmospheric or superatmospheric pressure (for example in a pressure range from 0.5 to 10 bar).

In general, 1 to 3 moles, preferably 1 to 1.5 moles, of the base are employed relative to 1 mole of indole. The indole is generally employed in an amount from 1 mole to 6 moles, preferably from 1 mole to 3 moles, relative to 1 mole of the aziridine.

The preparation of the N-sulphonylamidoethylindoles may be carried out, for example, as follows: the indole is dissolved in a solvent, and a base is added in portions. The aziridine is then added to the reaction solution. The work-up after completion of the reaction is carried out by extraction and/or chromatography.

The indoles of the general formula (IV) which are employed as starting materials are known or may be prepared by known methods [Houben-Weyl's "Methoden der organischen Chemie" (Methods of Organic Chemistry) 10/2, 570 ff]. The aziridines of the general formula (V) which are employed as starting materials are known or may be prepared from sulphonyl chlorides and ethylene imine by known methods [Howard; Marckwald Chem. Ber. 32, 2037].

The following may be used, for example, according to the invention as indoles: indole, 2-methylindole, 2-ethylindole, 2-isopropylindole, 5-chloroindole, 5-fluoroindole, 5-methylindole, 5-methoxyindole, 2-phenylindole, 6-methoxyindole, 6-fluoroindole, 6-chloroindole, 5-fluoro-2-methyl-indole and 5-chloro-2-methyl-indole.

The following may be used, for example, according to the invention as aziridines:
N-(4-methylphenyl)aziridine
N-(4-fluorophenyl)aziridine
N-(4-chlorophenyl)aziridine
N-(3-methylphenyl)aziridine
N-(3-fluorophenyl)aziridine
N-(3-chlorophenyl)aziridine The new indolypropionic acids and the salts thereof may be employed as active compounds in medicaments. The active compounds have a thrombocyte aggretation-inhibiting and thromboxane $A_2$ antagonistic action. They may preferably be employed for treatment of thrombosis, thromboembolism, ischaemia, as antiasthmatics and as antiallergics.

The new active compounds may be converted into the conventional formulations, such as tablets, dragees, pills, granules, aerosols, syrups, emulsions, suspensions and solutions, in a known fashion, using inert, nontoxic, pharmaceutically suitable excipients or solvents. The therapeutically active compound should in each case here be present in a concentration from about 0.5 to 90% by weight of the total mixture, that is to say in amounts which are sufficient to achieve the dosage latitude specified.

The formulations are prepared, for example, by extending the active compounds with solvents and/or excipients, if appropriate using emulsifiers and/or dispersing agents, it being possible, if appropriate, to use organic solvents as auxiliary solvents, for example in the case of the use of water as a diluent.

The following may be mentioned as examples of adjuvants: water, nontoxic organic solvents, such as paraffins (for example petroleum fractions), vegetable oils (for example groundnut/sesame seed oil), alcohols (for example: ethyl alcohol, glycerol), excipients, such as, for example, ground natural minerals (for example kaolins, aluminas, talc, chalk), ground synthetic minerals (for example highly disperse silicic acid, silicates), sugars (for example cane sugar, lactose and dextrose), emulsifiers (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

The application is carried out in a conventional fashion, preferably orally or parenterally, particularly perlingually or intravenously. In the case of oral administration, tablets may, of course, contain, in addition to the excipients mentioned, additives, such as sodium citrate, calcium carbonate and dicalcium phosphate, together with various aggregates, such as starch, preferably potato starch, gelatin and the like. Furthermore, lubricants, such as magnesium stearate, sodium lauryl sulphate and talc, may be used concomitantly for tablet production. In the case of aqueous suspensions, various flavor improvers or colarants, in addition to the abovementioned adjuvants, may be added to the active compounds.

In the case of parenteral administration, solutions of the active compounds may be employed using suitable liquid excipient materials.

In general, it has proven advantageous to administer amounts from about 0.001 to 1 mg/kg, preferably about 0.01 to 0.5 mg/kg, of body weight in the case of intravenous administration in order to achieve effective results, and the dosage for oral administration is about 0.01 to 20 mg/kg, preferably 0.1 to 10 mg/kg, of body weight.

Nevertheless, it may at times be necessary to deviate from the amounts mentioned, and in particular to do so as a function of the body weight and of the nature of the administration method, of the individual behavior towards the medicament, the nature of the formulation thereof, and the time of interval over which the administration takes place. Thus, it may suffice, in some cases, to manage with less than the abovementioned minimum amount, whereas in other cases the upper limit mentioned must be exceeded. Where relatively large amounts are administered, it may be advisable to divide these into several individul administrations over the course of the day.

Preparation examples de

EXAMPLE 1

N-[2-(Indol-1-yl)ethyl]-(4-methylphenyl)sulphonamide

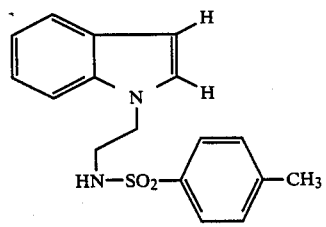

19.3 g (0.165 mol) of indole are dissolved in 50 ml of dimethylformamide and 5.28 g (0.176 mol) of 80% strength sodium hydride suspension in spindle oil are added in portions under nitrogen. When the hydrogen evolution is complete, 16.2 g (0.083 mol) of N-tosylaziridine are added to the reaction solution at 0° C. The reaction solution is stirred for a further 1 h at 0° C. and then for 1 h at room temperature. The solution is subsequently diluted carefully with water and extracted with ethyl acetate. The ethyl acetate phase is washed several times with water, dried using sodium sulphate and evaporated. The residue is subjected to chromatography on silica gel (0.040 to 0.063 mm, Merck) using a mixture of toluene and ethyl acetate in the ratio 9 to 1. A fraction is thus obtained which, after evaporation, yields 19.3 g (74.5 of theory) of a solid product.

$R_f$ value: 0.27 (toluene:ethyl acetate=9:1).
Melting point: 128°-130° C.

EXAMPLE 2

3{1-[2-[(4-Methylphenyl)sulphonamido]ethyl]indol-3-yl}-propionic acid

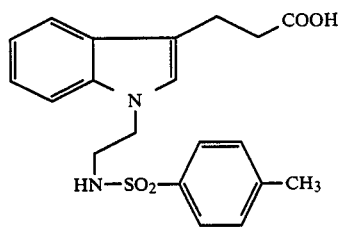

7.3 g (23.2 mmol) of N-[2-(indol-1-yl)ethyl]-(4-methylphenyl)sulphonamide are dissolved in a mixture of 14 ml of glacial acetic acid and 6 ml of acetic anhydride, and 4.6 g (63.9 mmol) of acrylic acid are added. The reaction solution is stirred for 3 h at 110° C. After cooling, the solution is diluted with ethyl acetate and extracted several times with 2N NaOH. The combined aqueous phases are extracted with ethyl acetate. This ethyl acetate phase is dried using sodium sulphate and evaporated. Thorough drying in a high vacuum yields 5.0 g (56% of theory) of an oily product. This oil is disslved in 30 ml of methanol and 0.7 g (13 mmol) of sodium methylate is added. Evaporation in vacuo and crystallization of the residue from ether produced 3.2 g of the crystalline sodium salt of the product.

$R_f$ value: 0.66 ($CH_2Cl_2/CH_3OH=9/1$).
Melting point: 125°-135° C. (Na salt).

The compounds listed in Table 1 were prepared analogously to Example 1:

TABLE 1

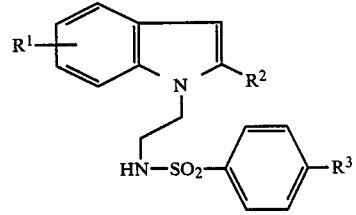

| No. | $R^1$ | $R^2$ | $R^3$ | $R_f$ value | Yield [%] | m.p. [°C.] |
|---|---|---|---|---|---|---|
| 3 | H | H | —F | 0.45[a] | 72.6 | oil |
| 4 | H | —CH₃ | —F | 0.45[a] | 76 | 110–112 |
| 5 | H | H | —Cl | 0.54[a] | 76.8 | 84–86 |
| 6 | H | —CH₃ | —Cl | 0.56[a] | 70 | 127–130 |
| 7 | 5-Cl | H | —F | 0.45[a] | 55.4 | 95–98 |
| 8 | H | —C₆H₅ | —Cl | 0.63[b] | 67 | 108–110 |
| 9 | 6-OCH₃ | H | —Cl | 0.42[a] | 75.3 | oil |

[a]toluene/ethyl acetate 8/2
[b]methylene chloride

The compounds listed in Table 2 were prepared analogously to Example 2

TABLE 2

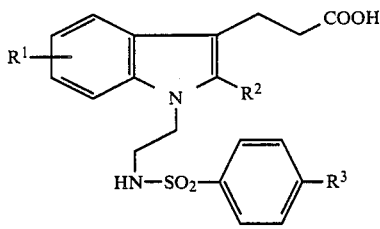

| No. | R¹ | R² | R³ | $R_f$ value | Yield [%] | m.p. [°C.] |
|---|---|---|---|---|---|---|
| 10 | H | H | —F | 0.32$^c$ | 23.7 | 170 Na salt |
| 11 | H | —CH₃ | —F | 0.5$^c$ | 49 | 170–90 Na salt |
| 12 | H | H | —Cl | 0.48$^c$ | 100 | 230–40 Na salt |
| 13 | H | —CH₃ | —Cl | 0.45$^c$ | 47 | 147–55 Na salt |
| 14 | 5-Cl | H | —F | 0.4$^c$ | 14.7 | 45–50 acid |
| 15 | H | —C₆H₅ | —Cl | 0.35$^a$ | 17.6 | 70–80 acid |
| 16 | 6-OCH₃ | H | —Cl | 0.29$^c$ | 9 | 184–5 acid |

$^a$toluene/ethyl acetate 8/2
$^c$CH₂Cl₂/CH₃OH 95/5

Use example

Blood from healthy subjects of both sexes was used in order to determine the thrombocyte aggregation-inhibiting action. One part of 3.8% strength aqueous sodium citrate solution as anticoagulant was admixed with 9 parts of blood. Platelet-rich citrated plasma (PRP) (Jürgens/Beller, Klinische Methoden der Blutgerinnungsanalyse [Clinical Methods for Blood Coagulation Analysis]; Thieme Verlag, Stuttgart, 1959) was obtained from this blood by centrifuging.

0.8 ml of PRP and 0.1 ml of the active compound solution were preincubated at 37° C. in a waterbath for these investigations. The thrombocyte aggregation was subsequently determined by the turbidometric method (Born, G.V.R., J. Physiol. (London), 162, 67, 1962) in an aggregometer at 37° C. (Therapeutische Berichte 47, 80–86, 1975). To this purpose, 0.1 ml of collagen, an aggregation-initiating agent, was added to the preincubated sample. Th e alteration of the optical density in the sample of the PRP was recorded over a period of 6 minutes and the deflection was determined after 6 minutes. To this purpose, the percentage inhibition compared to the control was calculated.

The range of the minimum effective concentration is specified as the limiting concentration (Table 3).

TABLE 3

| Example No. | Inhibition mg/l (limiting concentration) |
|---|---|
| 2 | 3–1 |
| 10 | 3–1 |
| 11 | 0.1–0.03 |
| 12 | 3–1 |
| 13 | 0.1–0.03 |

It is understood that the specification and examples are illustrative but not limitative of the present invention and that other embodiments within the spirit and scope of the invention will suggest themselves to those skilled in the art.

We claim:

1. An N-sulphonamidoethyl-indole of the formula

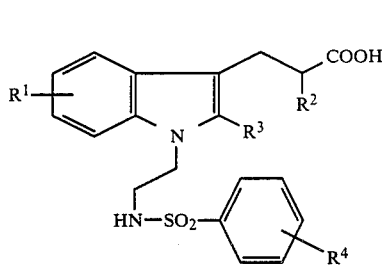

in which
R¹ represents hydrogen, C₁–C₄-alkyl, C₁–C₄-alkoxy, fluorine, chlorine, bromine, trifluoromethyl, C₁–C₄-alkylamino or di-C₁–C₄-alkylamino,
R² represents hydrogen or C₁–C₄-alkyl,
R³ represents hydrogen, C₁–C₄-alkyl or phenyl, and
R⁴ represents hydrogen, C₁–C₄-alkyl, C₁–C₄-alkoxy, fluorine, chlorine, bromine, trifluoromethyl, C₁–C₄-alkylamino or di-C₁–C₄-alkylamino. or a pharmacologically acceptable salt thereof.

2. A compound according to claim 1, wherein such compound is 3-[1-[2-[(4-methylphenyl)sulphonamido]ethyl]indol-3-yl]-propionic acid of the formula

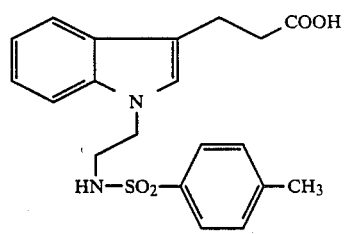

or a pharmacologically acceptable salt thereof.

3. A compound according to claim 1, wherein such compound is 3-[1-[2-[(4-fluorophenyl)sulphonamido]ethyl]indol-3-yl]-propionic acid of the formula

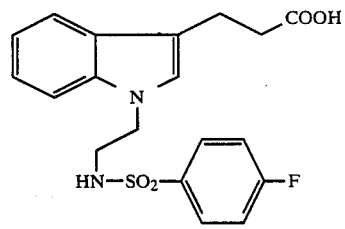

or a pharmacologically acceptable salt thereof.

4. A compound according to claim 1, wherein such compound is 3{2-methyl-1-[2-[(4-fluorophenyl)sulphonamido]ethyl]indol-3-yl}-propionic acid of the formula

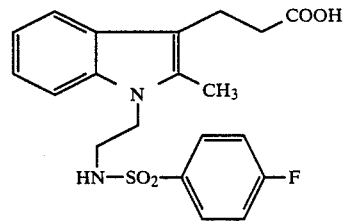

or a pharmacologically acceptable salt thereof.

5. A compound according to claim 1, wherein such compound is 3-[2-methyl-10[2-[(4-chlorophenyl)sulphonamido]ethyl]indo-3-yl]-propionic acid of the formula

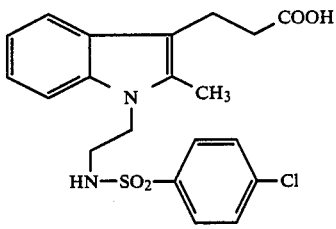

or a pharmacologically acceptable salt thereof.

6. A compound according to claim 1, wherein such compound is 3-{5-chloro-1-[2-[(4-fluorophenyl)sulphonamido]ethyl]indol-3-yl}-propionic acid of the formula

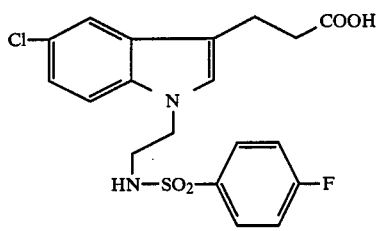

or a pharmacologically acceptable salt thereof.

7. A thrombocyte aggregation-inhibiting composition comprising an amount effective therefor of a compound or salt thereof according to claim 1 and a pharmacologically acceptable diluent.

8. A method of inhibiting aggregation of thrombocytes in blood or plasma which comprises adding thereto an aggregation-inhibiting amount of a compound or a pharmacologically acceptable salt thereof according to claim 1.

9. The method according to claim 8, wherein such compound is
3-[1-[2-[(4-methylphenyl)sulphonamido]ethyl]indol-3-yl]-propionic acid,
3-[1-[2-[4-fluorophenyl)sulphonamido]ethyl]indol-3-yl]-propionic acid,
3{2-methyl-1-[2-[4-fluorophenyl)sulphonamido]ethyl]indol-3-yl}-propionic acid,
3-[1-[2-[(4-chlorophenyl)sulphonamido]ethyl]indol-3-yl]-propionic acid or
3-{5-chloro-1-[2-[(4-fluorophenyl)sulphonamido]ethyl]indol-3-yl}-propionic acid,
or a pharmacologically acceptable salt thereof.

10. A compound of the formula

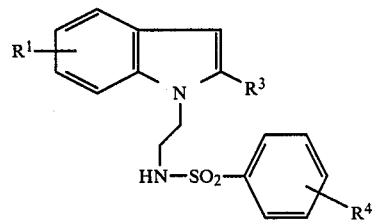

in which
$R^1$ represents hydrogen, $C_1$–$C_4$-alkyl, $C_1$–$C_4$-alkoxy, fluorine, chlorine, bromine, trifluoromethyl, $C_1$–$C_4$-alkylamino or di-$C_1$–$C_4$-alkylamino,
$R^3$ represents hydrogen, $C_1$–$C_4$-alkyl or phenyl, and
$R^4$ represents hydrogen, $C_1$–$C_4$-alkyl, $C_1$–$C_4$-alkoxy, fluorine, chlorine, bromine, trifluoromethyl, $C_1$–$C_4$-alkylamino or di-$C_1$–$C_4$-alkylamino.

* * * * *

UNITED STATES PATENT AND TRADEMARK OFFICE
CERTIFICATE OF CORRECTION

PATENT NO. : 4,843,091

DATED : June 27, 1989

INVENTOR(S) : Rosentreter et al.

It is certified that error appears in the above-identified patent and that said Letters Patent is hereby corrected as shown below:

Title Page, under "Abstract", line 4 from bottom     Delete "were" and substitute --where--

Title Page, under "Abstract", line 2 from bottom     Delete "thereat" and substitute --thereof--

Col. 8, line 26 and 27     Correct spelling of --aggregation--

Signed and Sealed this

Twentieth Day of November, 1990

Attest:

HARRY F. MANBECK, JR.

*Attesting Officer*     *Commissioner of Patents and Trademarks*